United States Patent [19]

Sasaki et al.

[11] 4,271,150

[45] Jun. 2, 1981

[54] UROKINASE PREPARATION FOR ORAL ADMINISTRATION

[75] Inventors: Koji Sasaki, Omiya; Yasukazu Harada, Tokyo, both of Japan

[73] Assignee: Zeria-Shinyaku Kogyo Kabushiki Kaisha, Tokyo, Japan

[21] Appl. No.: 18,239

[22] Filed: Mar. 7, 1979

[51] Int. Cl.³ ............................................. A61K 37/00
[52] U.S. Cl. ..................................................... 424/177
[58] Field of Search ................................... 424/94, 177

[56] References Cited

FOREIGN PATENT DOCUMENTS 52-96693 of 1977 Japan ......................................... 424/94

52-104013 of 1977 Japan ......................................... 424/94

OTHER PUBLICATIONS

Takada et al.—Chem. Abst. vol. 87 (1977), p. 206547p.

Primary Examiner—Delbert R. Phillips
Attorney, Agent, or Firm—Scrivener, Clarke, Scrivener and Johnson

[57] ABSTRACT

Disclosed is a urokinase preparation for oral administration which is effective for remedy of thrombosis such as cerebral thrombosis and cardiac infarction. This preparation comprises urokinase and, incorporated therein, glycoprotein.

2 Claims, 3 Drawing Figures

UROKINASE PREPARATION FOR ORAL ADMINISTRATION

DETAILED DESCRIPTION OF THE INVENTION

Figure 1:
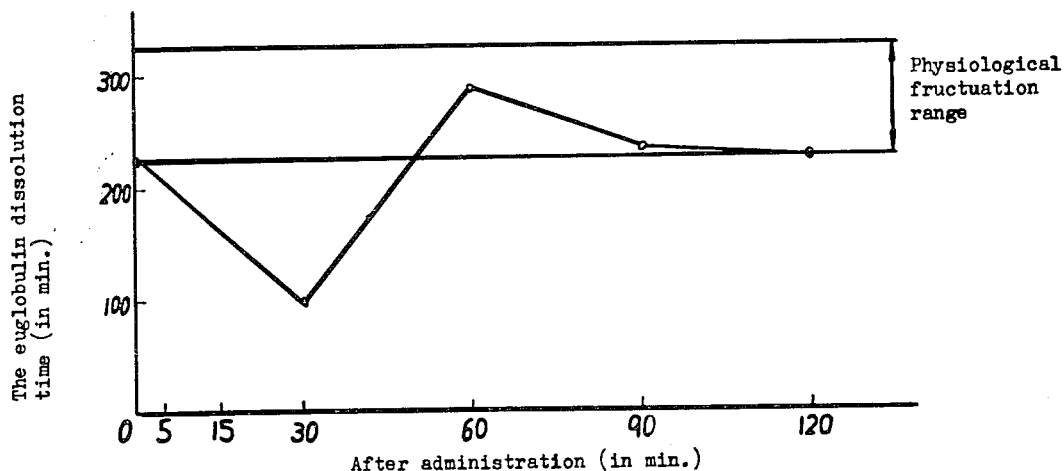

The present invention relates to a novel urokinase preparation, more particularly, a stable urokinase preparation for oral administration.

Urokinase is an enzyme extracted from human urine and has a function of converting plasminogen in blood to plasmin capable of enzymically decomposing fibrin. Accordingly, urokinase is effective for remedy of thrombosis such as cerebral thrombosis and cardiac infarction. It is known that when urokinase is used in combination with a carcinostatic agent, it exerts an effect of promoting the activity of the carcinostatic agent.

A conventional urokinase preparation is formed by freeze-drying, and at the time of administration, it is dissolved in a physiological salt solution or glucose injection solution and is administered by intravenous injection or instillation.

Ways of administering medicines for remedy of diseases are roughly classified into injection, oral administration and external application. From the view point of elimination of pains to patients and troubles to doctors, it is obvious that oral administration is most preferred if an effect comparable or superior to the effect attainable by injection can be expected by oral administration.

Especially in the case of urokinase, oral administration is significant because side effects such as fever by pyrogen are readily caused by intravenous injection of urokinase as is well-known in the art.

We, the inventors, examined the possibility of absorption of urokinase in the rectum: A physiological salt solution containing urokinase was directly administered to the rectum of a male rabbit having a body weight of 4 kg, and blood was sampled at predetermined intervals. The increase of the plasmin activity in blood was determined according to the euglobulin dissolution time method. When 30 minutes had passed from the administration, the dissolution time was shortened and the plasmin activity was increased. Thus, it has been confirmed that urokinase can be absorbed through the rectum. Accordingly, we considered that increase of the activity of plasmin could be expected also by oral administration of urokinase, and researches were made on oral administration of urokinase. As a result, it was found that there was a possibility of oral administration of urokinase.

However, since urokinase is ordinarily very unstable and is readily deactivated and the ratio of absorption of urokinase in the intestinal tracts is low, in order to enable oral administration of urokinase, it is necessary to stabilize urokinase to a level suitable for oral administration.

We made researches on stabilization of urokinase. As a result, it was found that when a glycoprotein such as mucin and mucoid is incorporated into urokinase, it can be stabilized to a level suitable for oral administration. More specifically, we noted that though purified urokinase is unstable, urokinase in urine or crude urokinase is relatively stable, and we expected that a substance contributive to stabilization of urokinase would be present in urine or crude urokinase. We furthered researches and found that glycoproteins present in urine, such as mucin and mucoid, are effective for stabilizing urokinase. It was also found that such glycoprotein acts as a so-called Castle's intrinsic factor and performs a function of promoting absorption of urokinase in the intestinal tracts in case of oral administration, and consequently is very effective for manifestation of pharmacological effects of urokinase in case of oral administration.

A primary object of the present invention is to provide a urokinase preparation suitable for oral administration which is effective for remedy of thrombosis and is comparable or superior in the curative effect to conventional urokinase preparations administered only by injection. In accordance with the present invention, this object can be attained by a urokinase preparation for oral administration which comprises urokinase and, incorporated therein, a glycoprotein.

The present invention will now be described in detail.

In the present invention, any type of urokinase can be used so far as it has a relative activity of 200 to 15,000 units per mg of protein. A freeze-dried product of urokinase for injection may be used in the present invention, and such freeze-dried product may contain minor amounts of harmless impurities.

As the glycoprotein to be incorporated into urokinase, there can be used not only glycoproteins contained in urine but also glycoproteins originating from animal organs, such as gastric mucin. Further, mucin that is one instance of the glycoproteins used in the present invention may be soluble mucin or hardly soluble mucin. As regards the amount of the glycoprotein to be incorporated in urokinase, for example in case of mucin or mucoid, satisfactory effects can be attained when mucin or mucoid is incorporated in an amount of about 1 to 2.5 mg per 500 units of urokinase.

The urokinase preparation for oral administration according to the present invention is prepared by mixing urokinase with a glycoprotein (together with appropriate additives) and filling the mixture into capsules or molding the mixture into tablets. In order to prevent decomposition or deactivation of urokinase by gastric juice, enteric coating may be formed on such capsules or tablets.

In the present invention, as is apparent from the foregoing illustration, by incorporating a glycoprotein such as mucin and mucoid into urokinase, the stability of urokinase is remarkably increased and absorption of urokinase from the intestinal tracts is effectively promoted in case of oral administration, and therefore, a urokinase preparation suitable for oral administration can be obtained. Further, the pharmacological effects (curative effect for thrombosis and effect of promoting the activity of a carcinostatic agent) possessed by urokinase can be exerted sufficiently with the aid of the incorporated glycoprotein. Thus, various advantages can be attained by the present invention.

The present invention will now be described by reference to the following examples.

EXAMPLE 1

In 10 ml of aqueous solution containing 5,000 units of urokinase is dissolved 25 mg of commercially available soluble mucin, and the solution is freeze-dried. Appropriate amount of lactose and mannitol are added to the resulting solid and the mixture is filled in gelatin capsules. Enteric coating is formed on the capsules.

EXAMPLE 2

To 20 ml of water are added 5,000 units of urokinase and 10 mg of commercially available, hardly soluble mucin, and the mixture is agitated to form a solution. The resulting solution is freeze-dried, and appropriate amounts of starch and lactose are added to the resulting solid. The mixture is molded into tablets and enteric coating is formed on the tablets.

EXAMPLE 3

In 10 ml of aqueous solution containing 5,000 units of urokinase is dissolved 25 mg of commercially available chondromucoid (crude sodium salt of condroitin sulfuric acid), and the solution is freeze-dried. Appropriate amounts of starch and lactose are added to the resulting solid, and the mixture is molded into tablets and enteric coating is formed on the tablets.

Figure 2:
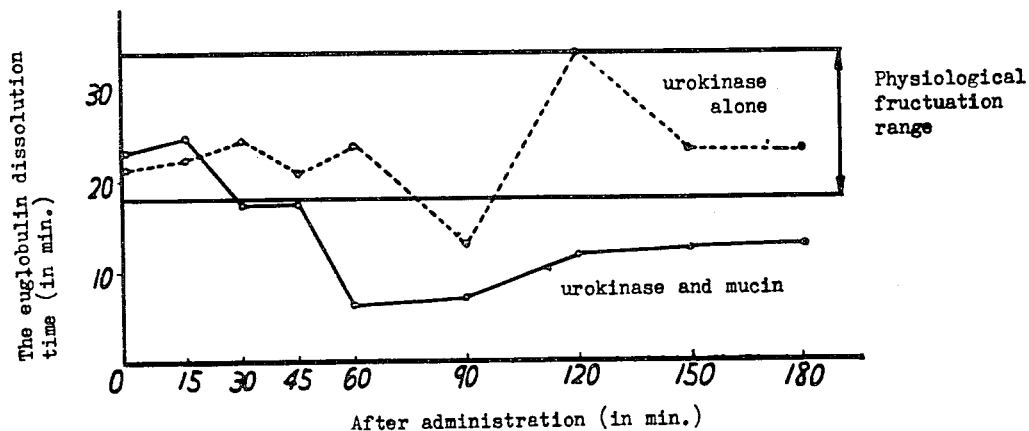
Figure 3:
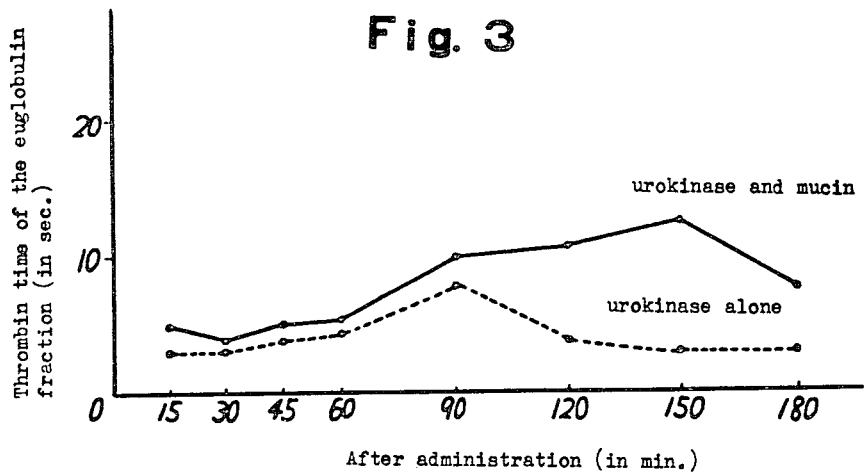

Experiments conducted so as to prove the effects of the present invention will now be described by reference to the accompanying drawings, in which:

FIG. 1 is a graph showing results of an absorption test where a physiological salt solution containing urokinase was directly administered to the rectum of a male rabbit having a body weight of 4 kg, blood was sampled at predetermined intervals and increase of the activity of plasmin in blood was measured according to the euglobulin dissolution time method; and FIGS. 2 and 3 are graphs showing results of absorption tests where urokinase alone and urokinase with mucin were orally administered, respectively.

EXPERIMENT 1

In this Experiment, the stability of urokinase was examined.

A solution was prepared by dissolving 25 mg of commercially available soluble mucin and 5,000 units of urokinase in 10 ml of a 0.1 M phosphate buffer solution (pH=7.4) according to the process described in Example 1. In the same manner, a mucin-free comparative solution was prepared. While both the solutions were allowed to stand at 37° C., the stability was determined according to Hestrin's method using TLMe as a substrate to obtain results shown in Table 1.

From these results, it is seen that in case of the solution containing urokinase alone, urokinase was completely deactivated when 120 minutes had passed but in case of the mucin-incorporated solution, the activity residual ratio was 60% when 120 minutes had passed. Thus, it has been confirmed that the stability of urokinase can be increased by incorporation of mucin.

TABLE 1

| sample | Urokinase Residual Activity Ratio (%) time elapsed (min.) | | | | |
|---|---|---|---|---|---|
| | 0 | 15 | 30 | 60 | 120 |
| urokinase alone (500 units/ml) | 100 | 36 | 31 | 18 | 11 |
| urokinase (500 units/ml) mucin (2.5 mg/ml) | 100 | 93 | 91 | 77 | 60 |

EXPERIMENT 2

Also in this Experiment, the stability of urokinase was examined.

In the same manner as described in Experiment 1, solutions were prepared by changing the mixing ratio of mucin to urokinase and the stability was tested while they were allowed to stand at 37° C. Obtained results are shown in Table 2. From these results, it is seen that the solution containing urokinase alone was completely deactivated when 4 hours had passed, whereas in case of the mucin-incorporated solution, a considerable activity residual ratio was attained even after passage of 4 hours. It is also seen that a relatively good stability was obtained when mucin was incorporated in an amount of 1 to 2.5 mg per 500 units of urokinase.

TABLE 2

| sample | Urokinase Activity Residual Ratio (%) time elapsed (hour) | | | | |
|---|---|---|---|---|---|
| | 0 | 1 | 2 | 3 | 4 |
| urokinase alone (500 units/ml) | 100 | 23 | 13 | 8 | 0 |
| urokinase (500 units/ml) mucin (0.25 mg/ml) | 100 | 81 | 73 | 53 | 27 |
| urokinase (500 units/ml) mucin (1.0 mg/ml) | 100 | 95 | 82 | 73 | 59 |
| urokinase (500 units/ml) mucin (2.5 mg/ml) | 100 | 93 | 87 | 73 | 64 |
| urokinase (500 units/ml) mucin (5.0 mg/ml) | 100 | 92 | 81 | 65 | 40 |

EXPERIMENT 3

Also in this Experiment, the stability of urokinase was examined.

In the same manner as described in Experiment 1, solutions were prepared by changing the mixing ratio of mucin to urokinase, and the solutions were heated at 37° C. for 30 minutes and they were allowed to stand still at 4° C. The stability was determined at predetermined intervals to obtain results shown in Table 3. From these results, it is seen that in case of urokinase alone, the activity was completely lost after passage of 96 hours, while in case of mucin-incorporated solutions, a considerable activity residual ratio was attained. Especially when 2.5 mg of mucin was incorporated in 500 units of urokinase, an activity residual ratio was as high as 60% even after passage of 96 hours.

TABLE 3

| sample | Urokinase Activity Residual Ratio (%) time elapsed (hour) | | | |
|---|---|---|---|---|
| | 0 | 24 | 72 | 96 |
| urokinase alone (500 units/10 ml) | 100 | 27 | 15 | 0 |
| urokinase (500 units/10 ml) mucin (0.25 mg/10 ml) | 100 | 86 | 65 | 34 |
| urokinase (500 units/10 ml) mucin (2.5 mg/10 ml) | 100 | 84 | 68 | 58 |
| urokinase (500 units/10 ml) mucin (25 mg/10 ml) | 100 | 80 | 42 | 30 |

EXPERIMENT 4

Also in this Experiment, the stability of urokinase was examined.

In the same manner as described in Experiment 1, solutions were prepared by incorporating chondromucoid into urokinase at various mixing ratios, and the stability was examined while the solutions were allowed to stand still at 37° C. Obtained results are shown in Table 4. From these results, it has been confirmed that the stability of urokinase can be increased by incorporation of chondromucoid. It is seen that when chondromucoid was incorporated in an amount of 1 to 2.5 mg per 500 units of urokinase, a relatively good stability was obtained.

TABLE 4

| sample | Urokinase Activity Residual Ratio (%) time elapsed (hour) | | | | |
|---|---|---|---|---|---|
| | 0 | 1 | 2 | 3 | 4 |
| urokinase alone (500 units/ml) | 100 | 22 | 11 | 7 | 0 |
| urokinase (500 units/ml) chondromucoid (0.25 mg/ml) | 100 | 70 | 61 | 48 | 23 |
| urokinase (500 units/ml) chondromucoid (1.0 mg/ml) | 100 | 89 | 81 | 72 | 61 |
| urokinase (500 units/ml) chondromucoid (2.5 mg/ml) | 100 | 96 | 88 | 79 | 67 |
| urokinase (500 units/ml) chondromucoid (5.0 mg/ml) | 100 | 91 | 82 | 69 | 57 |

EXPERIMENT 5

In this Experiment, preparations containing urokinase alone or urokinase and mucin were orally administered and absorption of urokinase was examined.

Preparations were formed in the same manner as in Example 1 by using 30,000 units of urokinase alone or in combination with 120 mg of mucin, and they were orally administered to a healthy male crossbred dog having a body weight of 4.3 kg. The euglobulin dissolution time and thrombin time of the euglobulin fraction were measured at predetermined intervals.

Results of the measurement of the euglobulin dissolution time are shown in FIG. 2. From these results, it is seen that when mucin was incorporated into urokinase, the euglobulin dissolution time was abruptly shortened after passage of about 60 minutes from the administration and the increased plasmin activity in blood was continued to the point when more than 180 minutes has passed from the administration, but when urokinase alone was administered, the dissolution time was shortened after passage of 90 minutes from the administration and increase of the plasmin level in blood was very slight.

Results of the measurement of the thrombin time of the euglobulin fraction are shown in FIG. 3. From these results, it is seen that when mucin was incorporated in urokinase, the thrombin time was prolonged after passage of 90 minutes from the administration and this effect was maintained to the point when 150 minutes had passed from the administration, but when urokinase alone was administered, only temporary prolongation of the thrombin time was observed when about 90 minutes had passed from the administration.

From the results of these Experiments, it has been confirmed that when a glycoprotein is incorporated into urokinase, the stability of urokinase can be remarkably increased over the stability of urokinase alone, and the absorption efficiency of urokinase at oral administration can be remarkably improved.

What is claimed is:

1. A method for treating thrombosis which comprises orally administering to a patient in need of such treatment an effective amount of urokinase in admixture with an effective urokinase stabilizing amount of a glycoprotein selected from the group consisting of mucins and mucoids which amount is effective in stabilizing urokinase against deactivation and in enhancing urokinase absorption from the gastrointestinal tract and a pharmaceutical carrier.

2. A method for treating thrombosis which comprises orally administering to a patient in need of such treatment an effective amount of urokinase in the form of a pharmaceutical composition for oral administration consisting of capsules or tablets coated with an enteric coating and comprising an effective amount of urokinase in admixture with an effective urokinase stabilizing amount of a glycoprotein selected from the group consisting of mucins and mucoids and a pharmaceutical carrier.

* * * * *